US006329540B1

(12) United States Patent
Kim et al.

(10) Patent No.: US 6,329,540 B1
(45) Date of Patent: Dec. 11, 2001

(54) VOLATILE ORGANOGALLIUM COMPOUND AND DEPOSITION OF GALLIUM NITRIDE FILM USING SAME

(75) Inventors: Yun-soo Kim; Chang-Gyoun Kim, both of Daejeon; Seung-Ho Yu, Kyungki-do, all of (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/594,298

(22) Filed: Jun. 15, 2000

(30) Foreign Application Priority Data

Jun. 15, 1999 (KR) .................................................. 99-22240

(51) Int. Cl.$^7$ ................................ C07F 5/00; C23C 16/34
(52) U.S. Cl. ...................... 556/1; 427/255.394; 427/590; 427/594
(58) Field of Search ................................ 556/1; 427/590, 427/593, 255, 394

(56) References Cited

U.S. PATENT DOCUMENTS

| 4,792,467 | * | 12/1988 | Melas et al. | 427/248.1 |
| 5,178,911 | * | 1/1993 | Gordon et al. | 427/255.2 |
| 5,650,198 | * | 7/1997 | Denbaars et al. | 427/255.2 |
| 6,017,774 | * | 1/2000 | Yuasa et al. | 438/46 |
| 6,106,899 | * | 8/2000 | Takamatsu et al. | 427/255.21 |

* cited by examiner

*Primary Examiner*—Porfirio Nazario-Gonzalez
(74) *Attorney, Agent, or Firm*—Anderson Kill & Olick, PC (57) ABSTRACT

A volatile organogallium compound of formula(I), an azidodialkylgallium complexed with a hydrazine derivative, can form a GaN film having no nitrogen defects by a metal organic chemical vapor deposition(MOCVD):

$$R^1R^2(N_3)Ga \cdot (R^3HNNR^4H) \qquad (I)$$

wherein, $R^1$ and $R^2$ are each independently $C_{1-5}$ alkyl; and $R^3$ and $R^4$ are each independently hydrogen or $C_{1-5}$ alkyl.

9 Claims, 8 Drawing Sheets

VOLATILE ORGANOGALLIUM COMPOUND AND DEPOSITION OF GALLIUM NITRIDE FILM USING SAME

FIELD OF THE INVENTION

The present invention relates to a novel, volatile organogallium compound; a process of the preparation thereof; and a metal organic chemical vapor deposition (MOCVD) process for forming a gallium nitride film on a substrate using said compound.

BACKGROUND OF THE INVENTION

GaN films are used in blue electroluminescent diodes and in generating blue laser. There have been reported studies to prepare such films by metal organic chemical vapor deposition (MOCVD) using such organogallium compounds as triethylgallium.amine adduct, bis(dialkyl-$\mu$-amido-gallium), bis[dimethyl(1,1-dimethylhydrazido)gallium] and the like (see J. E. Andrews and M. A. Littlejohn, *J. Electrochem. Soc.*, 122, 1273 (1975); U.S. Pat. No. 4,975,299 and European Patent Application 0 295 467 A2; and V. Lakhotia, D. A. Neumayer, A. H. Cowley, R. A. Jones and J. G. Ekerdt, *Chem. Mater.*, 7,546 (1995)).

However, as these GaN precursors exist in the form of dimers or trimers, which are often solids at room temperature, they are difficult to handle in MOCVD due mainly to their low vapor pressures. Further, these conventional precursors are known to give GaN films which have lattice nitrogen defects.

The present inventors have endeavored to develop a novel compound which can be employed in an improved MOCVD process for preparing a GaN film of improved quality, and have discovered that an azidodialkylgallium.hydrazine adduct has high volatility and can be effectively used in MOCVD to form a GaN film having no significant amount of nitrogen defects.

SUMMARY OF THE INVENTION

Accordingly, it is an object of the present invention to provide a novel organogallium compound which has high volatility and can be advantageously used in forming a GaN film of improved quality.

It is another object of the present invention to provide a process for preparing said compound.

It is a further object of the present invention to provide a process for depositing a GaN film on a substrate using said compound.

In accordance with one aspect of the present invention, there is provided an organogallium compound of formula(I):

$$R^1R^2(N_3)Ga \cdot (R^3HNNR^4H) \quad (I)$$

wherein, $R^1$ and $R^2$ are each independently $C_{1-5}$ alkyl; and $R^3$ and $R^4$ are each independently hydrogen or $C_{1-5}$ alkyl.

In accordance with another aspect of the present invention, there is provided a process for preparing a compound of formula(I) comprising the steps of: (a) reacting a compound of formula(II) with a compound of formula(III) to give a compound of formula(IV), and (b) reacting the compound of formula(IV) with sodium azide:

$$(R^3HNNR^4H) \cdot HX \quad (II)$$

$$R_3Ga \quad (III)$$

$$R_2(X)Ga \cdot (R^3HNNR^4H) \quad (IV)$$

wherein, X is halogen; $R^3$ and $R^4$ are the same as defined in formula(I) above; and R is $C_{1-5}$ alkyl.

In accordance with further another aspect of the present invention, there is provided a process for depositing a GaN film on a substrate which comprises bringing the vapor of the compound of formula(I) into contact with a substrate heated to a temperature ranging from 400 to 800° C.

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

The novel compound of formula(I) of the present invention is an azidodialkylgallium complexed with a hydrazine derivative, wherein the nitrogen atom of the azido group bonded to gallium is retained in the formation of a GaN film in MOCVD, while the other nitrogen atoms of the azido group are eliminated as $N_2$. The hydrazine ligand acts to prevent the compound of formula(I) from forming an oligomeric form.

Among the inventive organogallium compounds, azidodimethylgallium.methylhydrazine and azidodiethylgallium.methylhydrazine are preferred since they are liquids at room temperature.

In accordance with the present invention, the compound of formula(I) may be prepared by (a) reacting a compound of formula(II) with a compound of formula(III) to give a compound of formula(IV), and (b) reacting the compound of formula(IV) with sodium azide, as follows:

(a) $(R^3HNNHR^4) \cdot HX + R_3Ga \longrightarrow R_2(X)Ga \cdot (R^3HNNR^4H) + RH$
    (II)         (III)                    (IV)

(b) $R_2(X)Ga \cdot (R^3HNNR^4H) + NaN_3 \longrightarrow$
    (IV)

$$R_2(N_3)Ga \cdot (R^3HNNR^4H) + NaX$$
(I)

wherein, X, $R^3$, $R^4$ and R have the same meanings as defined above, and X is preferably chlorine, bromine or iodine.

In step (a), the compound of formula(II) is reacted with the compound of formula(III) in a stoichiometric ratio at a temperature ranging from −70 to 10° C. to obtain the compound of formula(IV). Further, in step (b), the compound of formula(IV) obtained in step (a) is reacted with sodium azide in a stoichiometric ratio at a temperature ranging from 70 to 100° C. to prepare the inventive organogallium compound of formula(I).

The reaction steps (a) and (b) may be respectively conducted in an organic solvent such as tetrahydrofuran, acetonitrile, diethylether, toluene and a mixture thereof, under an inert gas atmosphere.

The compound of formula(I) can be vaporized at a temperature ranging from 40 to 100° C. under a pressure ranging from $10^{-6}$ to $10^{-2}$ Torr.

In accordance with the present invention, a GaN film may be deposited on a substrate by bringing the vapor of the compound of formula(I) into contact with the surface of a substrate heated to a temperature ranging from 400 to 800° C.

The substrate which may be used in practicing the present invention is any inorganic solid that is stable at or above the film deposition temperature and examples thereof include glass, quartz, silicon, gallium arsenide, sapphire, alkali metal niobate and alkaline earth metal titanate, among which a single crystal of silicon is preferred when the coated substrate is intended for use in electronic applications.

The following Examples are given for the purpose of illustration only, and are not intended to limit the scope of the invention.

Synthesis of Chlorodialkylgallium.Hydrazine Derivatives (Compound(IV))

Preparation 1

Chlorodimethylgallium.hydrazine 1.0 g of hydrazine hydrochloride was suspended in tetrahydrofuran and 1.7 g of trimethylgallium was added thereto at 0° C. over a period of 15 minutes with stirring. The mixture was stirred at room temperature for 5 hours, and then, the solvent was removed under a reduced pressure. 2.1 g of the title compound was obtained in the form of a white solid having a melting point of 66° C.

The title compound thus obtained was subjected to $^1$H-NMR(acetonitrile-$d_3$, ppm): −0.30(s, 6H, Ga—CH$_3$) and 4.21(br, 4H, N—H).

Preparation 2

Chlorodimethylgallium.methylhydrazine

The procedure of Preparation 1 was repeated using 1.0 g of methylhydrazine hydrochloride and 1.4 g of trimethylgallium to obtain 1.8 g of the title compound in the form of a colorless liquid.

The title compound thus obtained was subjected to $^1$H-NMR(acetonitrile-$d_3$, ppm): −0.30(s, 6H, Ga—CH$_3$), 2.55(s, 3H, NCH$_3$) and 4.27(br, 3H, N—H).

Preparation 3

Chlorodimethylgallium.t-butylhydrazine

The procedure of Preparation 1 was repeated using 2.0 g of t-butylhydrazine hydrochloride and 1.8 g of trimethylgallium to obtain 2.7 g of the title compound in the form of a white solid having a melting point of 94° C.

The title compound thus obtained was subjected to $^1$H-NMR(acetonitrile-$d_3$, ppm): −0.28(s, 6H, Ga—CH$_3$), 1.09(s, 9H, NC(CH$_3$)$_3$) and 4.30(br, 3H, N—H).

Preparation 4

Chlorodiethylgallium.hydrazine

The procedure of Preparation 1 was repeated using 2.3 g of triethylgallium to obtain 2.5 g of the title compound in the form of a white solid having a melting point of 50° C.

The title compound thus obtained was subjected to $^1$H-NMR(acetonitrile-$d_3$, ppm): 0.38(quartet, 4H, Ga—CH$_2$CH$_3$), 1.06(t, 6H, Ga—CH$_2$CH$_3$) and 4.17(br, 4H, N—H).

Preparation 5

Chlorodiethylgallium.methylhydrazine

The procedure of Preparation 1 was repeated using 1.0 g of methylhydrazine hydrochloride and 1.9 g of triethylgallium to obtain 2.2 g of the title compound in the form of a colorless liquid.

The title compound thus obtained was subjected to $^1$H-NMR(acetonitrile-$d_3$, ppm): 0.38(quartet, 4H, Ga—CH$_2$CH$_3$), 1.06(t, 6H, Ga—CH$_2$CH$_3$), 2.55(s, 3H, N—CH$_3$) and 4.21(br, 3H, N—H).

Preparation 6

Chlorodiethylgallium.t-butylhydrazine

The procedure of Preparation 1 was repeated using 2.0 g of t-butylhydrazine hydrochloride and 2.5 g of triethylgallium to obtain 3.3 g of the title compound in the form of a white solid having a melting point of 90° C.

The title compound thus obtained was subjected to $^1$H-NMR(acetonitrile-$d_3$, ppm): 0.41(quartet, 4H, Ga—CH$_2$CH$_3$), 1.07(t, 6H, Ga—CH$_2$CH$_3$), 1.08(s, 9H, N—C(CH$_3$)$_3$) and 4.25(br, 3H, N—H).

Synthesis of Azidodialkylgallium.Hydrazine Derivatives (Compound(I))

EXAMPLE 1

Azidodimethylgallium.hydrazine 1.0 g of sodium azide was suspended in 10 mL of tetrahydrofuran and added thereto at room temperature with stirring was 10 mL of a tetrahydrofuran solution containing 1.0 g of chlorodimethylgallium.hydrazine obtained in Preparation 1. The mixture was refluxed for 12 hours and filtered using a glass filter. The resulting filtrate was distilled under a vacuum to remove the solvent and 0.8 g of the title compound was obtained in the form of a white solid having a melting point of 70° C.

The title compound thus obtained was subjected to $^1$H-NMR and FT-IR. $^1$H-NMR(acetonitrile-$d_3$, ppm) showed −0.40(s, 6H, Ga—CH$_3$) and 4.16(br, 4H, N—H), and FT-IR(ν(cm$^{-1}$), KBr pellet), 2076.

EXAMPLE 2

Azidodimethylgallium.methylhydrazine

The procedure of Example 1 was repeated using chlorodimethylgallium.methylhydrazine obtained in Preparation 2 to obtain 0.8 g of the title compound in the form of a colorless liquid.

The title compound thus obtained was subjected to $^1$H-NMR and FT-IR. $^1$H-NMR(acetonitrile-$d_3$, ppm) showed −0.39(s, 6H, Ga—CH$_3$), 2.54(s, 3H, N—CH$_3$) and 4.34(br, 4H, N—H), and FT-IR(ν(cm$^{-1}$), KBr pellet), 2080.

EXAMPLE 3

Azidodimethylgallium.t-butylhydrazine

The procedure of Example 1 was repeated using chlorodimethylgallium.t-butylhydrazine obtained in Preparation 3 to obtain 0.8 g of the title compound in the form of a white solid having a melting point of 95° C.

The title compound thus obtained was subjected to $^1$H-NMR and FT-IR. $^1$H-NMR(acetonitrile-$d_3$, ppm) showed −0.32(s, 6H, Ga—CH$_3$), 1.09(s, 9H, N—C(CH$_3$)$_3$) and 4.32(br, 3H, N—H), and FT-IR(ν(cm$^{-1}$), KBr pellet), 2084.

EXAMPLE 4

Azidodiethylgallium.hydrazine

The procedure of Example 1 was repeated using chlorodiethylgallium.hydrazine obtained in Preparation 4 to obtain 0.9 g of the title compound in the form of a white solid having a melting point of 97° C.

The title compound thus obtained was subjected to $^1$H-NMR and FT-IR. $^1$H-NMR(acetonitrile-$d_3$, ppm) showed 0.31(quartet, 4H, Ga—CH$_2$CH$_3$), 1.06(t, 6H, Ga—CH$_2$CH$_3$) and 4.00(br, 4H, N—H), and FT-IR(ν(cm$^{-1}$), KBr pellet), 2094.

EXAMPLE 5

Azidodiethylgallium.methylhydrazine

The procedure of Example 1 was repeated using chlorodiethylgallium.methylhydrazine obtained in Preparation 5 to obtain 0.8 g of the title compound in the form of a colorless liquid.

The title compound thus obtained was subjected to $^1$H-NMR and FT-IR. $^1$H-NMR(acetonitrile-d$_3$, ppm) showed 0.38(quartet, 4H, Ga—CH$_2$CH$_3$), 1.08(t, 6H, Ga—CH$_2$CH$_3$), 2.55(s, 3H, N—CH$_3$) and 4.32(br, 3H, N—H), and FT-IR(v(cm$^{-1}$), KBr pellet), 2085.

EXAMPLE 6

Azidodiethylgallium.t-butylhydrazine

The procedure of Example 1 was repeated using chlorodiethylgallium.t-butylhydrazine obtained in Preparation 6 to obtain 0.8 g of the title compound in the form of a white solid having a melting point of 46° C.

The title compound thus obtained was subjected to $^1$H-NMR and FT-IR. $^1$H-NMR(acetonitrile-d$_3$, ppm) showed 0.38(quartet, 4H, Ga—CH$_2$CH$_3$), 1.08(t, 6H, Ga—CH$_2$CH$_3$), 1.08(s, 9H, N—C(CH$_3$)$_3$) and 4.16(br, 3H, N—H), and FT-IR(v(cm$^{-1}$), KBr pellet), 2079.

Deposition of GaN Film

EXAMPLE 7

A Si(111) substrate was heated to 600° C. under an initial pressure of $1.0\times10^{-6}$ Torr. 0.5 g of azidodimethylgallium-.hydrazine prepared in Example 1 was vaporized at 80° C. and the vapor was conveyed to the surface of the substrate at a total pressure of $1.5\times10^{-4}$ Torr for 5 hours to deposit a film thereon.

The elemental composition of the deposited film surface determined by X-ray photoelectron spectroscopy corresponded to a Ga:N atomic ratio of 1:0.74. Further, an X-ray diffraction analysis showed that the deposited film was crystalline GaN.

EXAMPLE 8

A Si(111) substrate was heated to 600° C. under an initial pressure of $6.0\times10^{-7}$ Torr. 0.5 g of azidodimethylgallium-.methylhydrazine prepared in Example 2 was vaporized at 80° C. and the vapor was conveyed to the surface of the substrate at a total pressure of $5.0\times10^{-5}$ Torr for 5 hours to deposit a film thereon.

The elemental composition of the deposited film surface determined by X-ray photoelectron spectroscopy corresponded t a Ga:N atomic ratio of 1:0.7. Further, an X-ray diffraction analysis showed that the deposited film was crystalline GaN.

EXAMPLE 9

A Si(100) substrate was heated to 600° C. under an initial pressure of $6.0\times10^{-6}$ Torr. 0.5 g of azidodimethylgallium.t-butylhydrazine prepared in Example 3 was vaporized at 75° C. and the vapor was conveyed to the surface of the substrate at a total pressure of $1.0\times10^{-4}$ Torr for 5 hours to deposit a film thereon.

Figure 1:
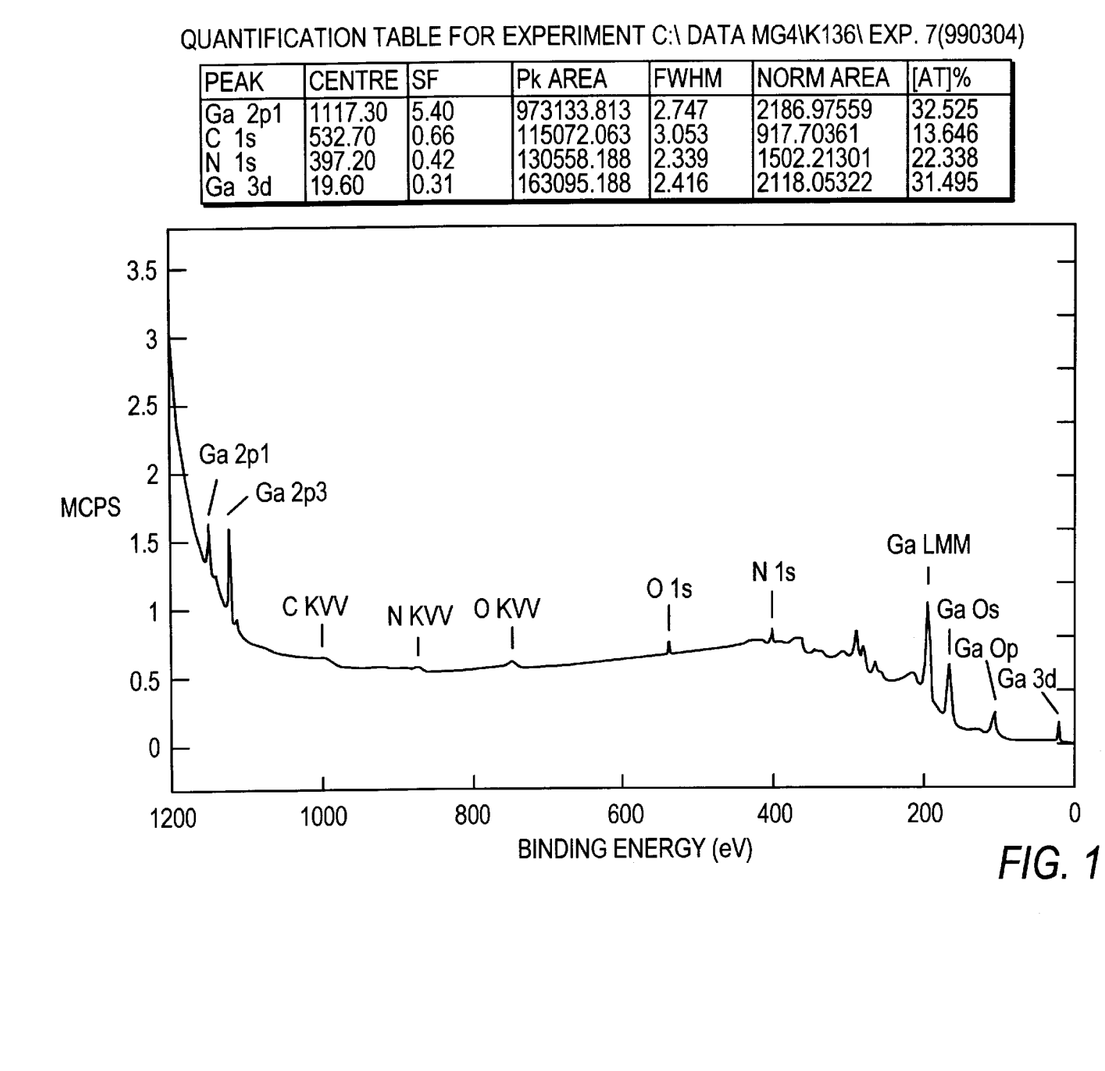
FIGS. 1 and 2: X-ray photoelectron and X-ray diffraction spectra of the GaN film obtained in Example 9, respectively.
Figure 2:
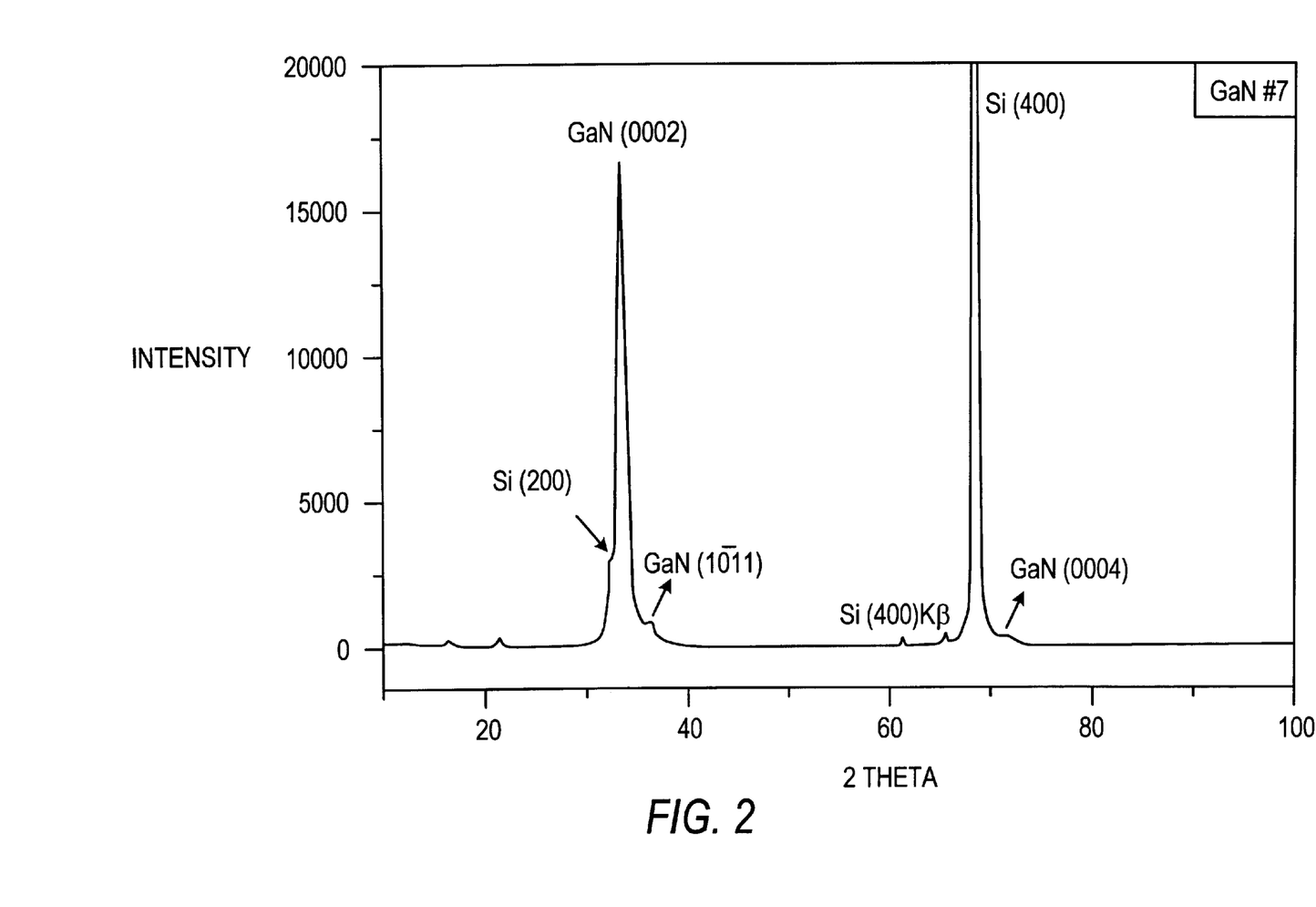

The elemental composition of the deposited film surface determined by X-ray photoelectron spectroscopy corresponded to a Ga:N atomic ratio of 1:0.71. Further, an X-ray diffraction analysis showed that the deposited film was crystalline GaN film preferentially oriented to the (002) direction. The X-ray photoelectron and X-ray diffraction spectra of the GaN film obtained in Example 9 are shown in FIGS. 1 and 2, respectively.

EXAMPLE 10

A Si(111) substrate was heated to 550° C. under an initial pressure of $1.0\times10^{-2}$ Torr. 0.5 g of azidodiethylgallium.hydrazine prepared in Example 4 was vaporized at 80° C. and the vapor was conveyed to the surface of the substrate at a total pressure of $1.5\times10^{-2}$ Torr for 9.5 hours to deposit a film thereon.

Figure 3:
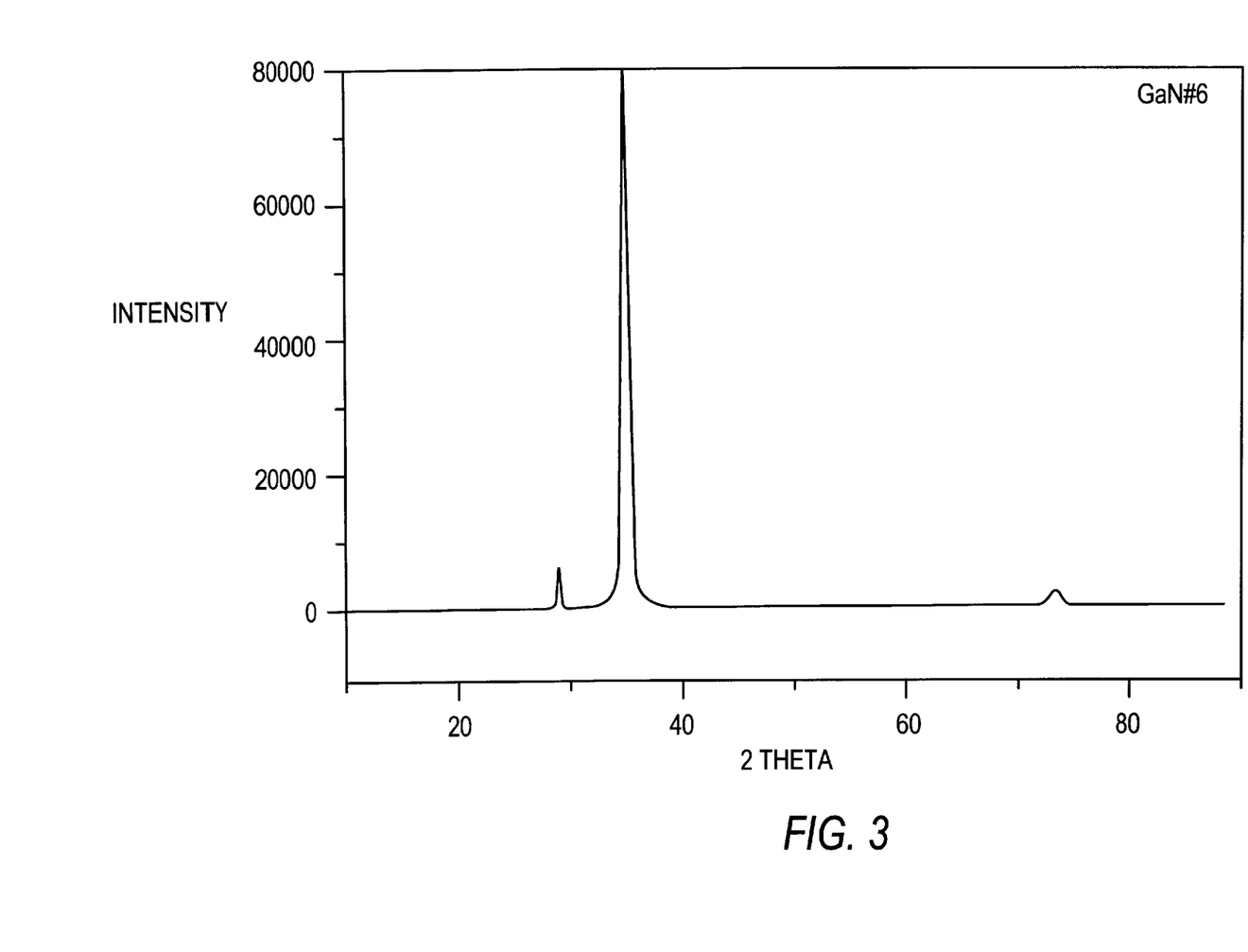
FIG. 3: X-ray diffraction spectrum of the GaN film obtained in Example 10.

The elemental composition of the deposited film surface determined by X-ray photoelectron spectroscopy corresponded to a Ga:N atomic ratio of 1:0.84. Further, an X-ray diffraction analysis showed that the deposited film was crystalline GaN preferentially oriented to the (110) direction. The X-ray diffraction spectrum of the GaN film obtained in Example 10 is shown in FIG. 3.

EXAMPLE 11

A Si(100) substrate was heated to 500° C. under an initial pressure of $2.0\times10^{-6}$ Torr. 0.5 g of azidodiethylgallium.methylhydrazine prepared in Example 5 was vaporized at 75° C. and the vapor was conveyed to the surface of the substrate at a total pressure of $4.0\times10^{-1}$ Torr for 3 hours to deposit a film thereon.

Figure 4:
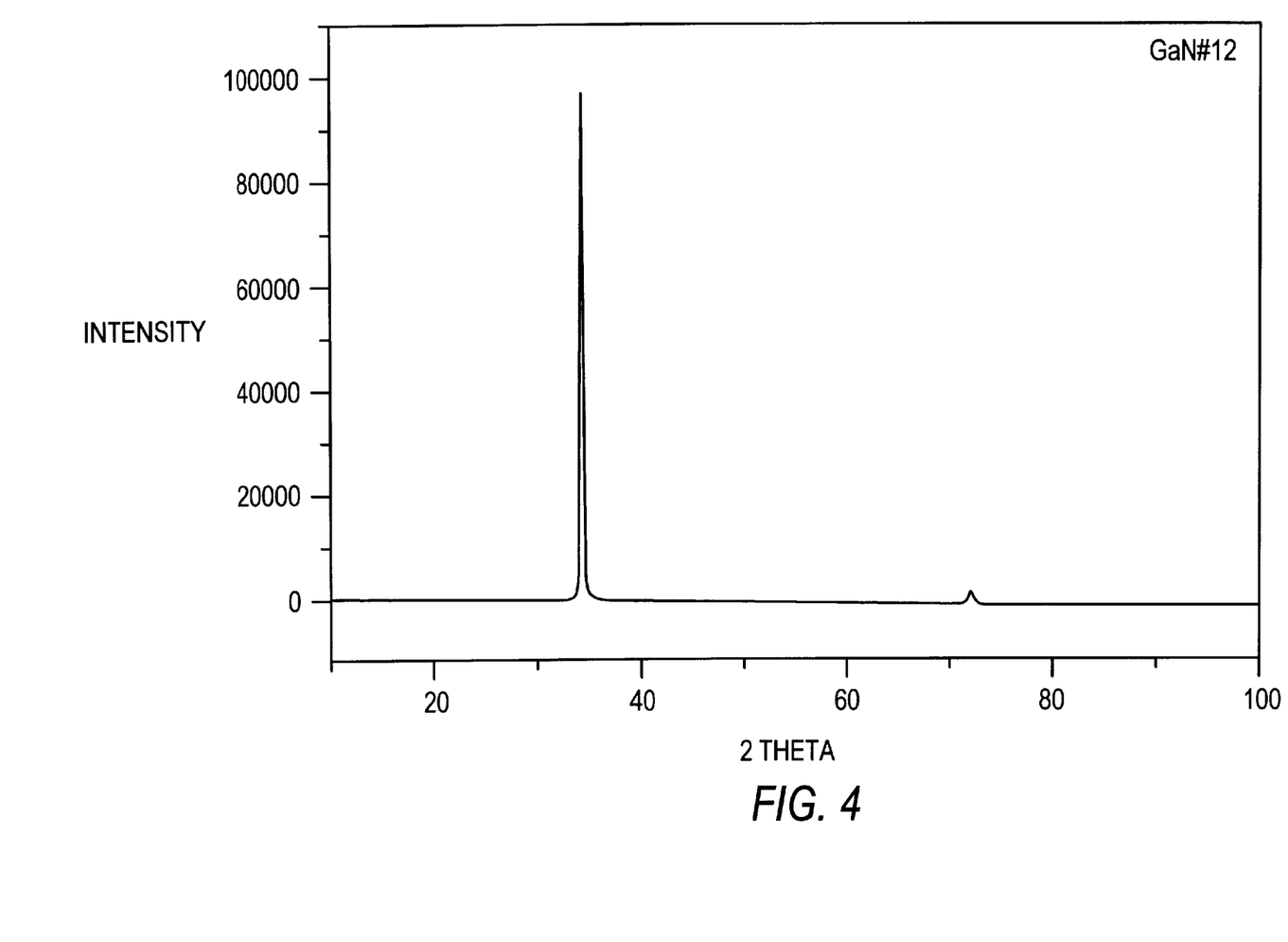
FIG. 4: X-ray diffraction spectrum of the GaN film obtained in Example 11.

The elemental composition of the deposited film surface determined by X-ray photoelectron spectroscopy corresponded to a Ga:N atomic ratio of 1:0.76. Further, an X-ray diffraction analysis showed that the deposited film was crystalline GaN preferentially oriented to the (002) direction. The X-ray diffraction spectrum of the GaN film obtained in Example 11 is shown in FIG. 4.

EXAMPLE 12

A Si(111) substrate was heated to 600° C. under an initial pressure of $2.0\times10^{-7}$ Torr. 0.5 g of azidodiethylgallium.methylydrazine prepared in Example 5 was vaporized at 75° C. and the vapor was conveyed to the surface of the substrate at a total pressure of $4.0\times10^{-4}$ Torr for 3 hours to deposit a film thereon.

Figure 5:
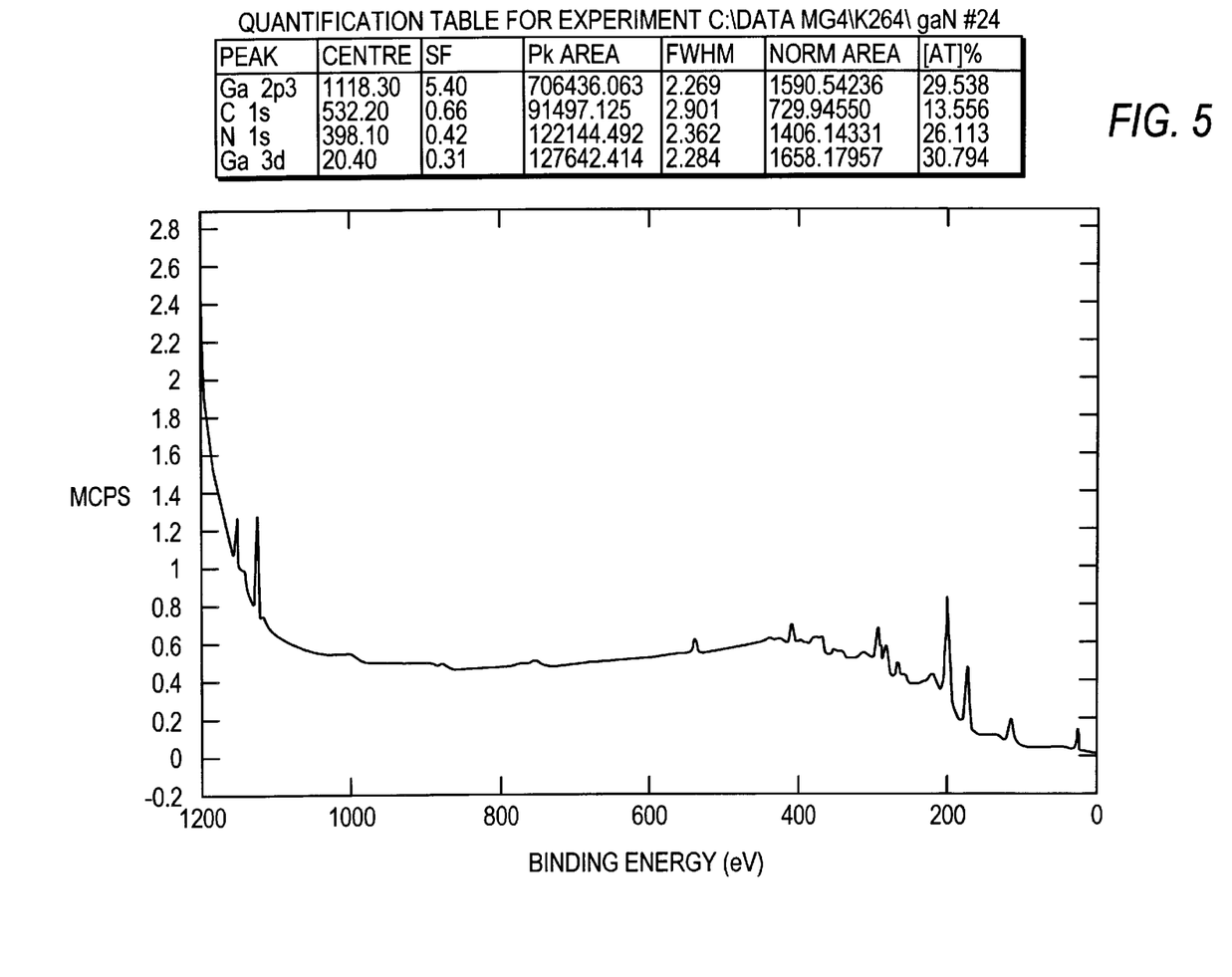
FIGS. 5 and 6: X-ray photoelectron and X-ray diffraction spectra of the GaN film obtained in Example 12, respectively.
Figure 6:
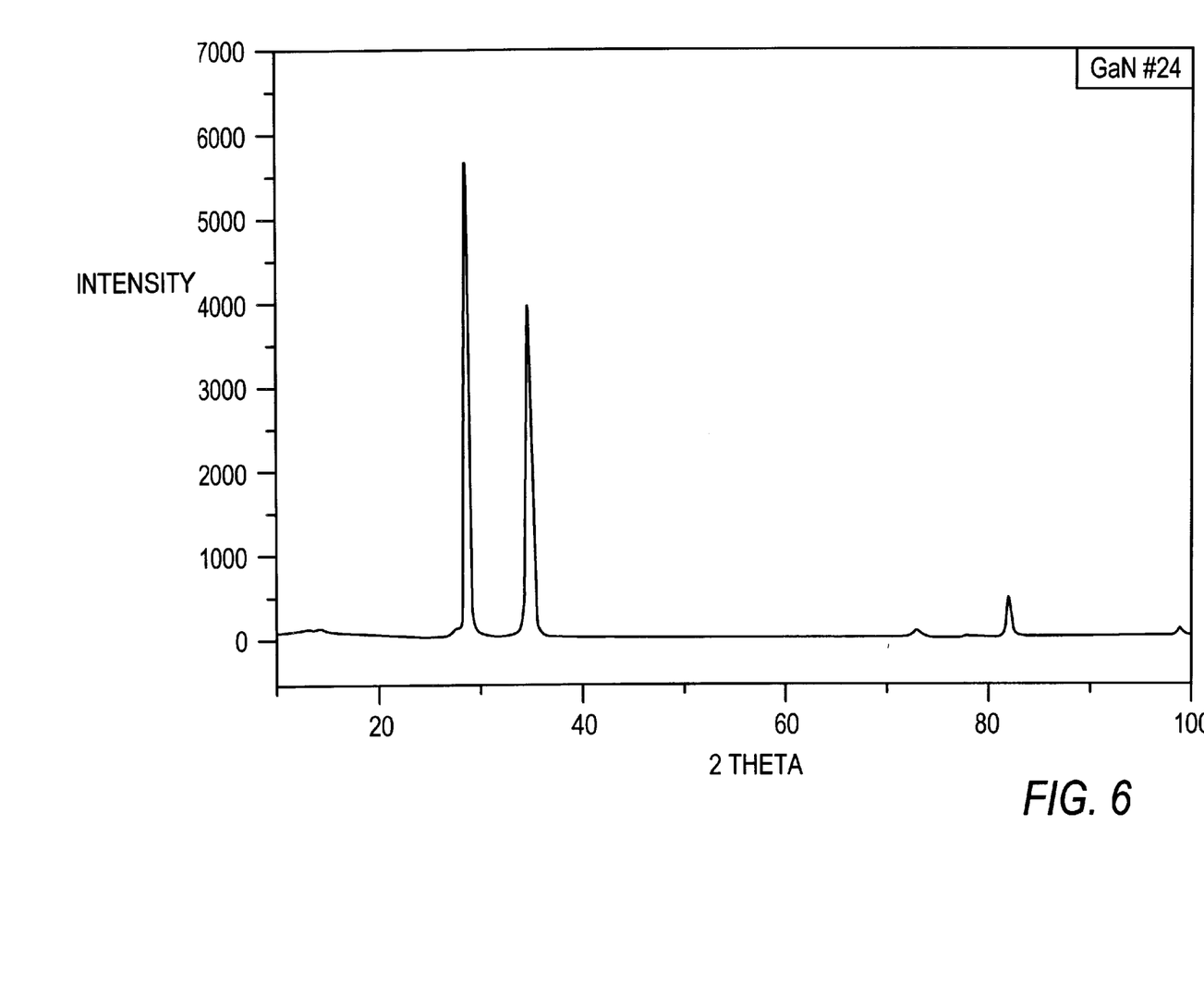

The elemental composition of the deposited film surface determined by X-ray photoelectron spectroscopy corresponded to a Ga:N atomic ratio of 1:0.77. Further, an X-ray diffraction analysis showed that the deposited film was crystalline GaN preferentially oriented to the (002) direction. The X-ray photoelectron and X-ray diffraction spectra of the GaN film obtained in Example 12 are shown in FIGS. 5 and 6, respectively.

EXAMPLE 13

A Si(100) substrate was heated to 500° C. under an initial pressure of $2.0\times10^{-7}$ Torr. 0.5 g of azidodiethylgallium.t-butylhydrazine prepared in Example 6 was vaporized at 75° C. and the vapor was conveyed to the surface of the substrate at a total pressure of $4.0\times10^{-4}$ Torr for 3 hours to deposit a film thereon.

Figure 7:
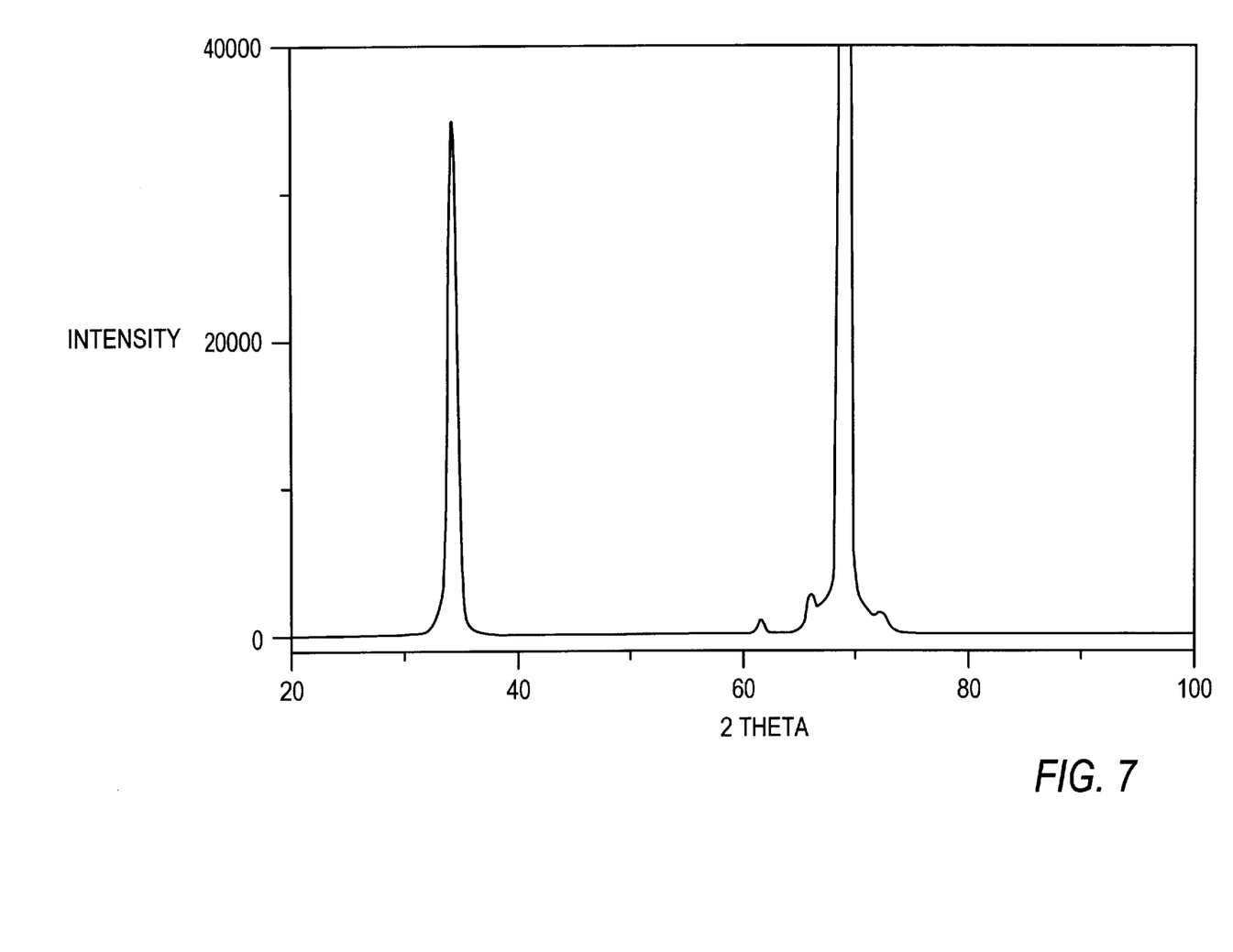
FIG. 7: X-ray diffraction spectrum of the GaN film obtained in Example 13.

The elemental composition of the deposited film surface determined by X-ray photoelectron spectroscopy corresponded to a Ga:N atomic ratio of 1:0.6. Further, an X-ray diffraction analysis showed that the deposited film was crystalline GaN. The X-ray diffraction spectrum of the GaN film obtained in Example 13 is shown in FIG. 7.

EXAMPLE 14

A Si(111) substrate was heated to 500° C. under an initial pressure of $1.0\times10^{-2}$ Torr. 0.5 g of azidodiethylgallium.t-butylhydrazine prepared in Example 6 was vaporized at 75°

C. and the vapor was conveyed to the surface of the substrate at a total pressure of $1.5 \times 10^{-2}$ Torr for 3 hours to deposit a film thereon.

Figure 8:
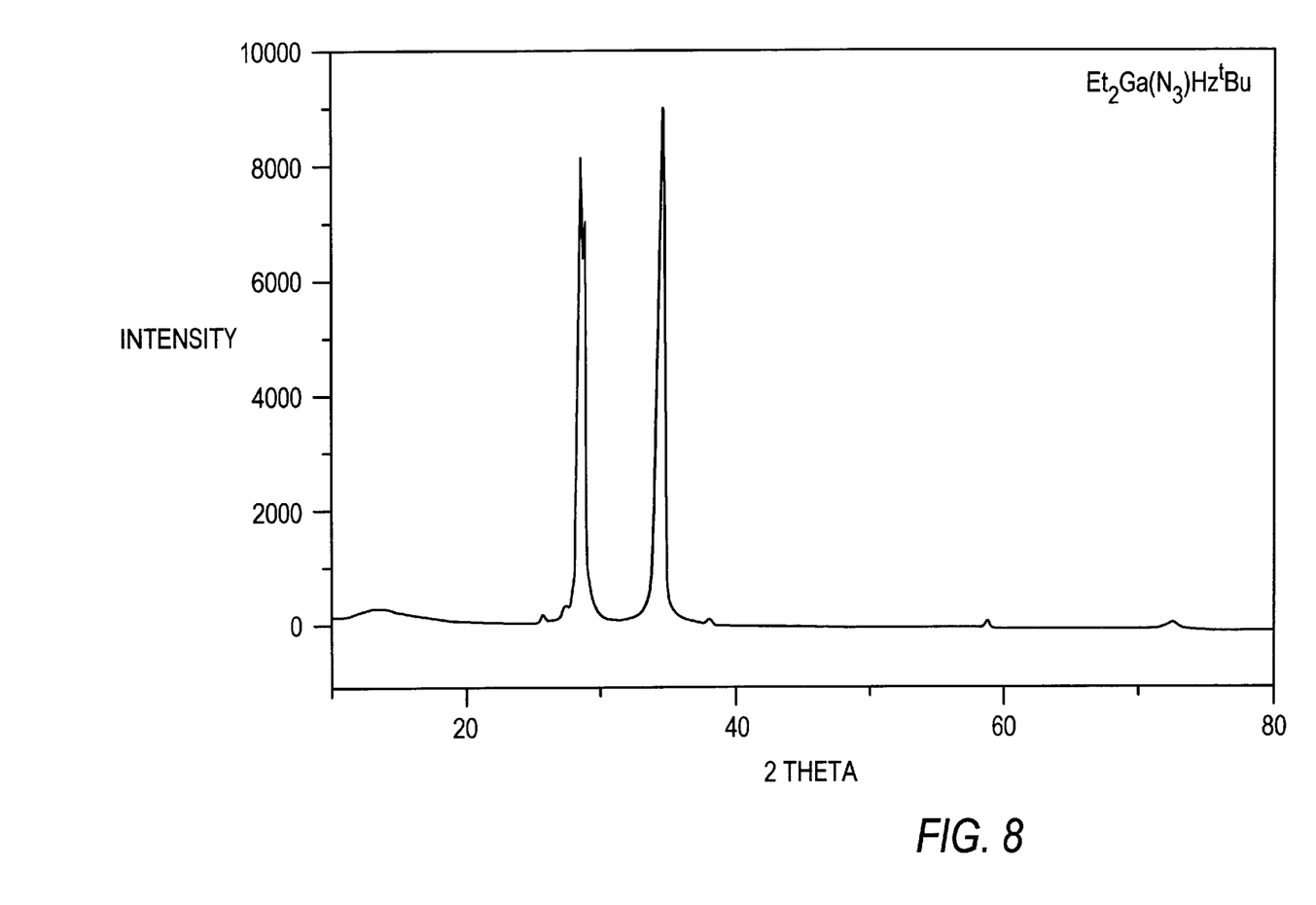
FIG. 8: X-ray diffraction spectrum of the GaN film obtained in Example 14.

The elemental composition of the deposited film surface determined by X-ray photoelectron spectroscopy corresponded to a Ga:N atomic ratio of 1:0.85. Further, an X-ray diffraction analysis showed that the deposited film was crystalline GaN. The X-ray diffraction spectrum of the GaN film obtained in Example 14 is shown in FIG. 8.

As shown above, the organogallium compound of the present invention can be vaporized at a low temperature, and therefore, it may be effectively employed in the MOCVD of a GaN film. In addition, the organogallium compound of the present invention may be advantageously used in preparing a GaN film having an improved quality which is suitable for a wide range of semiconductor devices such as blue electroluminescent diodes and blue laser materials.

While the embodiments of the subject invention have been described and illustrated, it is obvious that various changes and modifications can be made therein without departing from the spirit of the present invention which should be limited only by the scope of the appended claims.

What is claimed is:

1. An organogallium compound of formula(I):

$$R^1R^2(N_3)Ga.(R^3HNNR^4H) \quad (I)$$

wherein, $R^1$ and $R^2$ are each independently $C_{1-5}$ alkyl; and $R^3$ and $R^4$ are each independently hydrogen or $C_{1-5}$ alkyl.

2. The compound of claim 1, wherein $R^1$ and $R^2$ are the same.

3. The compound of claim 2, which is selected from the group consisting of azidodimethylgallium.hydrazine, azidodimethylgallium.methylhydrazine, azidodimethylgallium.t-butylhydrazine, azidodiethylgallium.hydrazine azidodiethylgallium.methylhydrazine and azidodiethylgallium.t-butylhydrazine.

4. A process for preparing the compound recited in claim 2, comprising the steps of:
   (a) reacting a compound of formula(II) and a compound of formula(III) to give a compound of formula(IV), and
   (b) reacting the compound of formula(IV) and sodium azide:

$$(R^3HNNHR^4).HX \quad (II)$$

$$R_3Ga \quad (III)$$

$$R_2(X)Ga.(R^3HNNR^4H) \quad (IV)$$

wherein, X is halogen; $R^3$ and $R^4$ are the same as defined in claim 1; and R is $C_{1-5}$ alkyl.

5. The process of claim 4, wherein step (a) is conducted in an organic solvent selected from the group consisting of tetrahydrofuran, acetonitrile, diethylether, toluene and a mixture thereof, at a temperature ranging from -70 to 10° C.

6. The process of claim 4, wherein step (b) is conducted in an organic solvent selected from the group consisting of tetrahydrofuran, acetonitrile, diethylether, toluene and a mixture thereof, at a temperature ranging from 70 to 100° C.

7. A process for depositing a GaN film on a substrate which comprises bringing the vapor of the compound of claim 1 into contact with a substrate heated to a temperature ranging from 400 to 800° C.

8. The process of claim 7, wherein the compound is vaporized at a temperature ranging from 40 to 100° C.

9. The process of claim 7, wherein the substrate is a single crystal of silicon.

* * * * *